United States Patent [19]

Crews et al.

[11] 4,244,837

[45] Jan. 13, 1981

[54] MULTI-PURPOSE BLOOD DILUENT FOR USE IN ELECTRONIC BLOOD ANALYSIS INSTRUMENTATION

[75] Inventors: Harold R. Crews, Miami; Dave Chastain, Jr., Ft. Lauderdale; Stephen Ledis, Hialeah, all of Fla.

[73] Assignee: Coulter Electronics, Inc., Hialeah, Fla.

[21] Appl. No.: 99,757

[22] Filed: Dec. 3, 1979

Related U.S. Application Data

[62] Division of Ser. No. 936,570, Aug. 22, 1978, Pat. No. 4,213,876.

[51] Int. Cl.³ .................. G01N 33/16; C09K 3/00
[52] U.S. Cl. ............................ 252/408; 23/230 B; 424/2; 424/3; 424/254; 424/258; 424/310; 435/4
[58] Field of Search .............. 252/408; 23/230 B; 424/2, 3, 254, 101, 258, 310; 435/4

[56] References Cited

U.S. PATENT DOCUMENTS

| | | | |
|---|---|---|---|
| 3,549,994 | 12/1970 | Rothermel et al. | 252/408 |
| 3,873,467 | 11/1975 | Scheide et al. | 252/408 |
| 3,873,467 | 3/1975 | Hunt | 252/408 |
| 3,920,580 | 11/1975 | Mast | 252/408 |
| 3,962,125 | 6/1976 | Armstrong | 252/408 |
| 3,977,995 | 8/1976 | Louderback et al. | 252/408 |
| 4,102,810 | 7/1978 | Armstrong | 252/408 |
| 4,179,398 | 12/1980 | Hunt | 252/408 |

OTHER PUBLICATIONS

Seeman, P., Biochem. Pharm., vol. 15, No. 11, pp. 1753-1766, (1966).
Fraser, R., et al., Biochem. J., vol. 147, pp. 401-410, (1975).
Baker, R. F., et al., Biochem. Biophys. Res. Communications, vol. 75, No. 2, pp. 381-388, (1977).
Palek, J., et al., Blood, vol. 50, No. 1, pp. 155-164, (1977).

*Primary Examiner*—Teddy S. Gron
*Attorney, Agent, or Firm*—Silverman, Cass & Singer, Ltd.

[57] ABSTRACT

A multi-purpose blood diluent especially suitable for use in electronic enumeration and sizing of blood cells, determination of hemoglobin concentration and their collective indices and platelet parameters in a single blood sample by means of suitable electronic instrumentation. The diluent is characterized as azide-free and capable of affording accurate, reproducible hematological test results from the said suitable electronic instrumentation. The diluent employs a chelating agent which functions as a bacteriostat and fungistat agent to prevent adverse growth of microorganisms, methohexital sodium barbituate as a compatible stabilizing agent for maintaining desired morphology of red blood cells, and an inorganic metallic sulfate for suppressing turbidity caused by abnormal globulins and/or high leukocyte counts which are encountered in certain blood samples. Because of the capability for use of the diluent in platelet determinations by the instrumentation, the diluent further is free of detergent action which would cause bubbles capable of interfering with the enumeration of platelets by the instrumentation. A modified and adjusted embodiment of the diluent enables its use in veterinary laboratory testing applications.

6 Claims, No Drawings

MULTI-PURPOSE BLOOD DILUENT FOR USE IN ELECTRONIC BLOOD ANALYSIS INSTRUMENTATION

This is a division of application Ser. No. 936,570 filed Aug. 22, 1978, now U.S. Pat. No. 4,213,876.

BACKGROUND OF THE INVENTION

This invention concerns a blood diluent especially suitable for use in electronic enumeration and sizing of blood cells, determination of hemoglobin and their collective indices and platelet parameters in a single blood cell sample by means of suitable electronic instrumentation. The diluent comprises a stable water solution of chemical salts providing an electrolytic solution to which a blood sample can be added so as to dilute the larger number of red blood cells, white blood cells, platelets and other blood components and enable the desired parameter of these blood components to be measured, counted and evaluated.

The invention also concerns the use of a modified embodiment of the diluent in veterinary laboratory testing applications.

It is a common medical diagnostic procedure to analyze and test a blood sample of a patient in order to make certain classic determinations with respect to the blood sample. This procedure is an important tool for the physician. Six characteristically important parameters are referred to as red blood cell count (RBC), the hematocrit (HCT), the hemoglobin (HGB), the mean corpuscular volume (HCV), the mean corpuscular hemoglobin (MCH), and the mean corpuscular hemoglobin concentration (MCHC). A seventh important determination is white blood cell count (WBC). An instrument which will accept a patient's blood sample and process the blood sample automatically and continuously to provide the parameters or determinations enumerated is described and claimed in U.S. Pat. No. 3,549,994. Said Pat. No. 3,549,994 provides acceptable definitions of said parameters and illuminates the problems to be solved in the handling of the blood sample as it is drawn through the fluid system of said patented apparatus.

Coulter Electronics, Inc. of Hialeah, Florida also manufactures and sells other blood cell counting and analyzing instruments which are less sophisticated than the apparatus of said U.S. Pat. No. 3,549,994, but which are operated to determine red blood cell and white blood cell count, hemoglobin concentration and their collective indices such as HCT, MCV, MCH and MCHC. The multi-purpose diluent embodying the invention is suitable for use with such instrumentation as well, where problems attendant the successful handling of the blood sample are the same. In other words, this blood diluent is compatible with other electronic particle analysis instruments utilizing the so-called Coulter principle. Such instruments may be referred to herein, at times, selectively by the registered trademark "COULTER COUNTER ®" owned by Coulter Electronics, Inc.

In U.S. Pat. No. 3,962,125 issued for the invention "Multi-Purpose Diluent For Use In Blood Analysis By Electronic Instrumentation Of The Coulter Type", there is described and claimed a diluent especially suitable for eliminating the problems attendant the use of prior blood diluents which use sodium azide as the effective bacteriostatic agent. Pat. No. 3,962,125 illuminates further the characteristics of red blood cells which must be taken into account in order to provide a practical and suitable diluent.

The diluent of U.S. Pat. No. 3,962,125 did not focus on suitability thereof for use in making platelet parameter determinations. At the time of the invention of said Patent No. 3,962,125, Coulter Electronics, Inc. had marketed an instrument known as the Model "S" and Model "S"-Sr. which did not have the capability for making platelet determinations. Consequently, the diluent of U.S. Pat. No. 3,962,125 was not concerned with the critical factor of bubble formation by reason of detergent action thereof which would cause bubbles capable of interfering with the enumeration of platelets by electronic instrumentation capable of making such determinations. Since that time, Coulter Electronics, Inc. has introduced electronic instrumentation known as the Model "S"-Plus which does have platelet determination capability and in connection with the multi-purpose diluent embodying the invention is especially suitable for dilution of blood samples which are drawn through such instruments during its operation.

SUMMARY OF THE INVENTION

The invention provides a multi-purpose, electrolytic solution for use in hematological enumeration of blood cells, the determination of hemoglobin concentration and other important parameters of a blood sample and platelet determinations by means of automated electronic particle analysis apparatus of the type manufactured by Coulter Electronics, Inc. of Haileah, Florida and marketed as its Model "S"-Plus. The solution is osmotically balanced for mean cell volume stability, is azide free and contains methohexital sodium barbiturate as a stabilizer agent for maintaining the desired morphology of red blood cells. The solution contains a metallic sulfate for suppressing turbidity caused by abnormal globulins and/or high leukocyte counts which are encountered in certain blood samples and is characterized by being free of detergent action which would cause bubbles capable of interfering with the enumeration of platelets by the electronic instrumentation.

The invention also includes a modified and adjusted embodiment of the diluent solution which enables it to be used in veterinary medicine laboratory testing applications.

The invention provides a blood diluent which can be used successfully with the electronic instrumentation of Coulter Electronics, Inc. and which is compatible with their present calibration for making such hematological analysis.

The blood diluent embodying the invention successfully substitutes a non-toxic and more compatible bacteriostatic agent for sodium azide without diminution in effectiveness. Further, the diluent is osmotically balanced and unreactive so as to eliminate any interference with the required chemical conversion of hemoglobin materials to cyanmethemoglobin for proper hemoglobin concentration determinations contemplated by the apparatus in question.

Further, the blood diluent embodying the invention is free of detergent action which would contribute to formation of bubbles in the instrumentation which would interfere with making the platelet determinations desired for the instrument.

DESCRIPTION OF PREFERRED FORMULATION

An example of the multi-purpose blood diluent embodying the invention is as follows:

| Ingredient | Approximate Amounts |
|---|---|
| Sodium chloride anhydrous | 5 gms/L |
| Sodium dihydrogen phosphate . $H_2O$ | 0.2 gms/L |
| Disodium phosphate . 7 $H_2O$ | 2.0 gms/L |
| Sodium sulfate anhydrous | 10 gms/L |
| 8-Quinolinol (8-hydroxyquinoline) | 0.145 gms/L |
| Methohexital sodium barbituate | 0.125 gms/L |
| Distilled $H_2O$ | Sufficient quantities to produce 1 liter |

The diluent specified above was adjusted to a pH of 7.2 to 7.6 by a suitable buffering agent which constituted the phosphate salt. The osmolality of the blood diluent was maintained at 316 to 330 milliosmoles/Kg. 8-hydroxyquinoline citrate can be substituted for 8-hydroxyquinoline with the additional advantage of more ready dissolution. The amount of the citrate ingredient used would be 0.145 gms/L. Likewise, potassium dihydrogen phosphate and dipotassium phosphate can be substituted, respectively,, for the sodium phosphate salts.

The desired characteristic of osmotic balance is procured through the use of sodium chloride. The diluent is totally unreactive and osmotically balanced for mean cell volume with use of procaine hydrochloride and phosphate salts for buffering effectiveness. Methohexital sodium barbiturate, like procaine hydrochloride, serves to stabilize the red blood cell volume. Sodium sulfate serves to eliminate turbidity due to elevated white blood cell counts which affects hemoglobin determinations.

The bacteriostatic agent which replaces the sodium azide is 8-quinolinol or 8-quinolinol citrate. The bacteriostatic agent has low toxicity and hence completely eliminates the problem of possible adverse toxic effect supplicable to laboratory technicians as would be the case with the use of sodium azide. Also, 8-quinolinol or 8-quinoline citrate does not form any known hazardous substances with copper or lead commonly used in water drainage systems. Acceptable substitutes were found to be 8-hydroxyquinaldine (2-methyl-8-quinolinol),8-hydroxyquinoline-5-sulfonic acid-dihydrate and 8-hydroxy-5-nitroquinoline, all being from the family of hydroxyquinolines.

It has been known to use the procaine hydrochloride alone in larger amounts in diluent reagents of this type. However, such larger amounts resulted in undesirable hemolysis. We believe that the use of 8-quinolinol as a chelating agent in the presence of procaine hydrochloride for maintaining red cell morphology was not known or expected to be effective as a blood diluent used in this environment. These ingredients were found to be most compatible in the subject diluent and performed their respective functions without interference one with the other Methohexital sodium barbiturate in the same relative amount as procaine hydrochloride, was found to act in the same way as the procaine hydrochloride described in Ser. No. 936,570 of which this application is a division.

Like procaine hydrochloride, mepivacaine hydrochloride and lidocaine hydrochloride, methohexital sodium barbiturate is known generally to act as an anesthetic and was found to be compatible with the family of hydroquinoline compounds.

The desired characteristic of osmotic balance is procured through the use of sodium chloride, an expedient already known in connection with such blood diluents. The diluent is totally unreactive and osmotically balanced for mean cell volume with the use of procaine hydrochloride and phosphate salts for buffering effectiveness. The methohexital sodium barbiturate serves to stabilize the red blood cell volume. The sodium sulfate serves to eliminate turbidity due to elevated white blood cell counts which affects hemoglobin determinations.

Further, the blood diluent embodying the invention is suitable for use in diluting blood samples for making platelet determinations. In its activity to suppress growth of microorganisms, no small bubbles are produced as is the case with use of other bacteriostatic agents. Such small bubbles where produced in an electronic instrument for making platelet determinations could result in the bubbles being misinterpreted as small particles, such as platelets. Consequently, by reason of the fact that the blood diluent embodying the invention does not generate small bubbles during its bacteriostatic and fungistatic activities, the blood diluent is especially useful in electronic instruments such as the COULTER COUNTER ® Model "S"-Plus now available on the market.

Another advantage of the blood diluent by reason of its capability of being used in electronic instrumentation is that it is not corrosive with respect to segmenting and transferring valves found in the COULTER COUNTER ® Model "S"-Plus instrument. There is produced a blood diluent embodying the invention which is an electrolyte capable of conducting current, which stabilizes the red blood cells so that their cubic volume can be accurately measured, which has no adverse effect on white blood cells and can function as an electrolyte for counting white blood cells and platelets by electronic methodology, has no adverse effect on blood platelets and does not interfere with the conversion of hemoglobin to the cyanmethemoglobin form in which hemoglobin is measured.

Preparation of the diluent does not require any special procedures or any special order of addition of ingredients to the water. Consequently, the invention does not concern any methodology in formulation of the diluent. The mixture of ingredients is done mechanically by moderate stirring over suitable periods of time. The solution is then filtered through a 0.2 micron filter and storable in suitable containers directly. Consequently, the cost of manufacture is modest and advantageous because it does not involve critical and expensive procedures.

Although preferred formulation has been specified above, the range of pH and osmolality may be broadened for useful purposes. Thus, the pH range may be maintained from between a pH of 7.2–7.6. likewise, the useful range of osmolality may be between 316 and 330 milliosmoles. This can be accomplished by varying the amount of active ingredients used for the purpose as specified herein.

The blood diluent embodying the invention provides for advantages which are additional to and not found in the blood diluent described and claimed in U.S. Pat. No. 3,962,125 and is especially adapted for use with a blood sample which is passed through an electronic particle analyzer of the general type manufactured by Coulter electronics, Inc. of Hialeah, Florida. Long term stability studies of the diluent invention reveal no microbial growth and no detergent action giving rise to interfering bubbles was encountered. No harmful effects on components of the instruments were encountered.

The diluent embodying the invention can be adapted for use in veterinary medicine as follows:

(a) quantity of sodium chloride anhydrous is reduced to 3.75 gms/liter.

(b) pH is adjusted to a pH of between 7.0 and 7.6 by a suitable buffering agent, such as, a phosphate salt.

(c) osmolality is maintained at between 285–300 milliosmoles/kg.

What it is desired to claim is:

1. A multi-purpose blood diluent suitable for use in electronic enumeration and sizing of blood cells, determination of hemoglobin concentration and their collective indices and platelet parameters in a single blood sample by means of electronic instrumentation comprising:

A. An osmotically balanced solution of sodium chloride, a monobasic phosphate salt, a dibasic phosphate salt and sodium sulfate,
   B. a hydroxyquinoline as a bacteriostatic agent,
   C. methohexital sodium barbiturate for maintaining desired red blood cell morphology during operation of said instrumentation,
   D. said diluent being an aqueous electrolytic solution maintained within a preselected range of pH and osmolality.

2. The blood diluent of claim 1 in which said bacteriostatic agent consists of a compound selected from the group of 8-hydroxyquinoline, 8-hydroxyquinoline citrate, 8-hydroxyquinaldine, 8-hydroxy-5-nitroquinoline and 8-hydroxyquinoline-5-sulfonic acid dihydrate.

3. The blood diluent of claim 1 in which said bacteriostatic agent comprises 8-quinolinol.

4. The blood dilulent of claim 1 in which the pH range is between 7.2 and 7.6.

5. The blood diluent of claim 4 in which the osmolality range is between 316 and 330 milliosmoles.

6. The blood diluent of claim 1 in which phosphate salts are sodium phosphate salts.

* * * * *